(12) United States Patent
Langeveld et al.

(10) Patent No.: US 7,462,464 B1
(45) Date of Patent: *Dec. 9, 2008

(54) METHOD FOR THE DETECTION OF ANTIMICROBIAL RESIDUES IN FOOD AND BODILY FLUID SAMPLES

(75) Inventors: Pieter Cornelis Langeveld, Delft (NL); Jacobus Stark, Rotterdam (NL); Petrus Andreas Van Paridon, Voorburg (NL)

(73) Assignee: DSM IP Assets B.V. (NL)

( * ) Notice: Subject to any disclaimer, the term of this patent is extended or adjusted under 35 U.S.C. 154(b) by 1141 days.

This patent is subject to a terminal disclaimer.

(21) Appl. No.: 10/089,874

(22) PCT Filed: Oct. 3, 2000

(86) PCT No.: PCT/EP00/09874

§ 371 (c)(1),
(2), (4) Date: Sep. 3, 2002

(87) PCT Pub. No.: WO01/25471

PCT Pub. Date: Apr. 12, 2001

(30) Foreign Application Priority Data

Oct. 4, 1999 (EP) .................................. 99203264
Oct. 18, 1999 (EP) .................................. 99203429

(51) Int. Cl.
*C12Q 1/18* (2006.01)
*C12Q 1/02* (2006.01)
*C12N 1/20* (2006.01)

(52) U.S. Cl. ...................... 435/32; 435/29; 435/252.5; 435/253.4

(58) Field of Classification Search ................... 435/32, 435/29, 252.5, 253.4, 252.3
See application file for complete search history.

(56) References Cited

U.S. PATENT DOCUMENTS 3,941,658 A * 3/1976 Lameris et al. ................ 435/32
5,354,663 A * 10/1994 Charm et al. ................. 435/32

FOREIGN PATENT DOCUMENTS

EP 0 005 591 * 12/1979
EP 0 285 792 * 10/1988

* cited by examiner

*Primary Examiner*—Jon P Weber
*Assistant Examiner*—Rosanne Kosson
(74) *Attorney, Agent, or Firm*—Nixon & Vanderhye P.C.

(57) ABSTRACT

The present invention relates to a novel method for the rapid detection of the presence or absence of antimicrobial residues in products preferably food products.

16 Claims, No Drawings

METHOD FOR THE DETECTION OF ANTIMICROBIAL RESIDUES IN FOOD AND BODILY FLUID SAMPLES

This application is the U.S. national phase of International Application No. PCT/EP00/09874, filed on Oct. 3, 2000, which claims priority to Application Nos. EP 99203264.9, filed on Oct. 4, 1999, and EP 99203429.8, filed on Oct. 18, 1999.

FIELD OF THE INVENTION

The present invention relates to a novel method for the rapid detection of the presence or absence of antimicrobial residues in products preferably food products. A one step test method is described in which residues of antimicrobial compounds such as antibiotics are detected while disturbing compounds, such as natural pigments (e.g. blood) and naturally inhibiting compounds (e.g. lysozyme) present in the samples, which may interfere with the test, are inactivated. These compounds are inactivated after combining the sample with the test.

DESCRIPTION OF THE PRIOR ART

The presence of antimicrobial residues in food and feed is a growing concern among the consumers due to health-related problems and the increase of drug resistant bacteria. Antibiotics are not only applied as medication, but also widely used as antimicrobial growth promoting substances.

Antimicrobial residues might be present in e.g. body liquids, organs, meat and eggs which are used for consumption. Antimicrobial residues might also be present in food products in which the said animal products are added as an ingredient. Examples of food products are milk; meat of cow, pig, poultry and fish; sea food such as shrimps; liver, processed meat products such as sausages; ready to eat meals and baby food. Antimicrobial residues might also be present in body liquids or animal tissues, which are suitable for examination by for example food-inspection authorities. Examples are blood, kidney tissue or pre-urine obtained from the kidney and urine. Urine and blood are suitable for examination prior to slaughtering of the animal.

It is well known that concentrations of antimicrobial residues in animal body liquids, animal tissues and food products may be too high. In most countries, such as the countries of the European Union, Canada and the United States, Maximum Residue Levels (MRL) are regulated by legislation.

Test methods to detect antimicrobial residues in milk products such as microbial inhibition tests (e.g. agar diffusion tests) or methods making use of selective binders (e.g. antibodies or tracers) are well known. Examples of microbiological test methods have been described in GB-A-1467439, EP 0005891, DE 3613794, CA 2056581, EP 0285792 and U.S. Pat. No. 5,494,805. These documents all deal with ready to use tests that make use of a test organism. The test organism is mostly imbedded in an agar medium, which may contain an indicator, a buffer solution, nutrients and substances to change the sensitivity for certain antimicrobial compounds in a positive or negative way.

Examples of suitable test organisms are strains of *Bacillus, Streptococcus* or *E. coli*. In general, the principle of these tests is that when antibacterial compounds are present in a sample at a concentration sufficient to inhibit the growth of the test organism the colour of an acid/base or redox indicator will remain the same. However, when no inhibition occurs, growth of the test organism is accompanied by the formation of acid or reduced metabolites leading to a change in the colour of the indicator.

These test methods are suitable for the detection of antimicrobial residues in many food products. However up to now detection of antimicrobial residues in samples (e.g. some types of milk such as individual cow milk, liver, urine, kidney, meat juice, eggs), which contain a high concentration of natural antimicrobial substances (e.g. lysozyme, lactoferrin, lactoperoxidase) or a high concentration of natural pigments (e.g. blood), has not been easy to perform.

The inhibiting substances referred to above show inhibitory activity against the test microorganism leading to false positive results (Okada et al., Journal of the Japan Veterinary Medical Association 46: (2) 103-107 (1993); Schiffmann, Methodische und rechtliche Probleme beim Nachweis von Hemmstoffen in Milch, Publisher Tierarztliche Hochschule, Hannover, Germany; Weisser, Tierarztliche Umschau 31: (6) 276-278 (1976); Heinert et. al., Archiv für Lebensmittelhygiene 27: (2) 55-60 (1976); Carlsson et. al., Milchwissenschaft 42: (5) 282-285 (1987); Carlsson et al., Journal of Dairy Science 72: (12) 3166-3175 (1989)).

Natural inhibiting substances present in samples can be inactivated by heating, e.g. at 80° C. for 10 minutes (Vermunt et. al., Netherlands Milk and Dairy Journal 47: (1) 31-40 (1993); Weisser, Tierarztliche Umschau 31: (6) 276-278 (1976)) or by using well known dialysis methods (Takahiro, Shokuhin Eiseigaku Zasshi 24: (4) 423-428 (1983); van Wall, Archiv fur Lebensmittelhygiene 29: (6) 235 (1978)). After this pretreatment the sample can be used for further testing by following the procedures of the test. In case of a microbial agar diffusion test (e.g. as described in EP 0005891) the liquid sample can be added directly to the test, after which the test is incubated.

Natural pigments (e.g. blood) present in the sample (e.g. meat juice or juice obtained from organs) will always interfere with the agar matrix. In the case of tests based on a colour shift using e.g. an acid/base or redox indicator, the presence of such natural pigments often leads to an unreadable test. A method to diminish the effect of the natural pigments is to carry out a pre-incubation. In case of an agar diffusion test according to the method described in EP 0005891, the sample (e.g. meat fluid) is added to the test, followed by a pre-incubation of, e.g. 10-30 minutes, at room temperature. This pre-incubation should be long enough to let the antimicrobial residues diffuse into the agar matrix. After the pre-incubation the sample is removed, the test is washed with water and incubated following the instructions of the manufacturer. However, the methods require extra time and handling and will not prevent diffusion of disturbing compounds such as natural pigments into the agar. Even worse in case where a heating step (inactivation of natural inhibitors) is included, a brown colour always appears, making the test results even more unreadable. Mistakes in reading the results of the test may lead to both false positive and false negative results.

Moreover laboratories executing studies concerning the presence or absence of antimicrobial residues in foods are limited by the time available to execute these studies. With the present time consuming methods only a very limited amount of samples can be examined. Further, these assays can only be executed in well-equipped laboratories and by well-educated persons, which is also a limiting factor.

It can be concluded that up to now no suitable test methods for detecting antimicrobial residues in samples containing high concentration of natural inhibiting compounds and/or natural pigments have been available. The present methods are time consuming and may lead to both false positive and false negative results, which leads to unacceptable amounts of antibiotics in the food chain and to economic losses.

DETAILED DESCRIPTION OF THE INVENTION

The present invention now seeks to provide a reliable and simple to carry out one-step test for the detection of antimicrobial residues in liquid samples which might contain natural inhibitors and/or disturbing compounds such as natural pigments.

It has been found that when such a sample is added to a test suitable for detecting antimicrobial residues and then incubated for a sufficient time at a sufficient temperature to inactivate the natural inhibiting compounds of the sample, the test can be incubated directly after heating to determine the presence or absence of antimicrobial residues.

According to another aspect of the invention it has also been found that a suitable thickening agent can be added to the liquid sample, and disturbing compounds present in the sample can be caught in the matrix. Said matrix is preferably formed during the heating step.

It is even more surprising that antimicrobial residues diffuse directly from the solid matrix into the test system. Thus, additional extraction methods to obtain the antimicrobial residues from the matrix are not required.

According to the invention there is thus provided a process for determining the presence or absence of an antimicrobial residue in a sample, which process comprises:
  (i) contacting the sample with a test suitable for determining the presence or absence of an antimicrobial residue in the sample;
  (ii) treating the contacted sample and test for a sufficient time interval to inactivate a natural disturbing compounds present in the sample; and
  (iii) incubating the contacted sample and test.

By natural disturbing compounds are meant compounds which may disturb the test and which are naturally present in the sample such as naturally inhibiting compounds (e.g. lysozyme) or natural pigments (e.g. blood). Thus by disturbing or inhibiting is meant the behaviour of these compounds on part of the test, for example the test microorganism or the colour indicators.

The invention also provides a test kit for determining the presence or absence of an antimicrobial residue in a sample, which test kit comprises:
  (i) a test suitable for determining the presence or absence of an antimicrobial residue in a sample; and
  (ii) a sample, wherein a natural inhibiting substance present in the sample has been inactivated.

The invention also provides a test kit for determining the presence or absence of an antimicrobial residue in a sample, which test kit comprises:
  (i) a test suitable for determining the presence or absence of an antimicrobial residue in a sample; and
  (ii) a thickening agent.

Any test suitable for determining the presence or absence of antimicrobial residues may be in used in a process or test kit of the invention. Suitable tests are those in which selected sensitive microorganisms are used, e.g. microbial agar diffusion tests, or tests based on selective binding of the compound to be detected. Selective binding can be achieved using the well-known antibody technology or by using specific tracers. An example of a specific tracer is the penicillin binding protein, which is used in e.g. the Delvo-X-Press® for detecting beta-lactams.

Examples of suitable microbial agar diffusion tests are tests in which species of *Bacillus, Streptococcus* or *E. coli* are used. Preferably thermophilic species, e.g. *Bacillus stearothermophilus* and *Streptococcus thermophilus* are used. Examples of preferred strains are *Bacillus stearothermophilus* var. *calidolactis* C953 (deposited with the Laboratory of Microbiology of the Technical University of Delft under the accession number LMD 74.1 in 1974 and with the Centraal Bureau voor Schimmelcultures (CBS), Baam under the accession number CBS 760.83 in 1983 were the strain is available to the public) and *Streptococcus thermophilus* T101 (DSM 4022, deposited on Mar. 3, 1987). Both strains are very sensitive to antimicrobial compounds, especially chemotherapeutics such as sulfa compounds and antibiotics such as penicillins and tetracyclines. *E. coli* strains or other suitable gram-negative bacteria can be used for the detection of e.g. quinolones.

*Bacillus stearothermophilus* var. *calidolactis* C953 and *Streptococcus thermophilus* T101 are fast growing and have the advantage that they are thermophilic. For example the optimum growth temperature of said *Bacillus* strain is from 50° to 70° C. The test organism is therefore very suitable for a test according to the invention as it is not killed by heating to inactivate the natural inhibiting compounds which may be present in the sample.

When the test organism is a *Bacillus* strain, it is preferably incorporated into the agar medium in the form of a spore suspension which may be prepared and incorporated into the agar medium prior to solidification by known methods (see for example GB-A-1467439). When the test organism is a *Streptococcus* strain, the bacteria are preferably incorporated into the agar medium in the form of bacterial cells which may be prepared according to known methods (see for example EP 0285792). The concentration of the test organism in the agar medium is preferably from $10^5$ to $10^{10}$ colony forming units per ml of agar medium.

Suitable nutrients to enable multiplication of the test organism in the absence of antimicrobial residues are for example assimilable carbon sources (e.g. lactose, glucose or dextrose), assimilable nitrogen sources (e.g. peptone) and sources of growth factors, vitamins and minerals (e.g. yeast extract).

The growth of the test microorganism can be detected using well known methods, preferably by colour change of the agar medium of the test sample. Typically a colour indicator, preferably an acid-base or a redox indicator, is used. Examples of suitable acid-base indicators include bromocresol purple and phenol red. Examples of suitable redox indicators include brilliant black, methylene blue, toludine blue and nile blue. Also combinations of two or more indicators can be used.

Typically, a solid matrix is a matrix which retains disturbing compounds, for example pigments, but which also allows antimicrobial residues in the sample, to diffuse in the test.

Optionally the sensitivity of the test may be altered by adding certain substances, by changing the test conditions such as pH or concentration of buffering substances or agar or by varying the ratio of the volumes of agar and the sample. Examples of substances that may be added to the test system to change sensitivity are nucleosides such as adenosine, or antifolates such as trimethoprim, ormethoprim or tetroxoprim, which improve the sensitivity of the test organism to sulfa compounds. Salts of oxalic acid or hydrofluoric acid may be added to improve the sensitivity to tetracyclines. Cysteine may be added to diminish the sensitivity to penicillins.

Samples suitable for use in the invention include any substance for which the absence or presence of antimicrobial residues is to be determined. For example the sample may be an animal body fluid, an animal tissue or an extract, for example a liquid extract thereof. In addition, the sample may be a foodstuff. Examples of animal body fluids include blood, urine, pre-urine, milk and meat juice. Examples of animal tissues include muscle, heart, liver and kidney. The sample may be an extract of one of those tissues.

The amount of liquid sample to be added to the test depends on the test system. For microbial diffusion tests typically from 0.01 to 1.0 ml, preferably from 0.05 to 0.5 ml is added to the test using well-known methods.

According to one embodiment of the invention a suitable thickening agent can be added to the sample. Examples of suitable thickening agents for use in a process or test kit of the invention are, for example polysaccharides (e.g. cellulose such as methylcellulose, HMPC, locust bean gum, starch or xanthan) or proteins (e.g. egg albumin, whey proteins or bovine albumin). Preferably methylcellulose and bovine albumin are used. Also combinations of suitable thickening agents can be used. The concentration of the suitable thickening agent should be sufficient to form a solid matrix.

According to another embodiment of the invention, inhibiting compounds are inactivated by a temperature treatment. For example the sample/test is heated for about 10 minutes at about 80° C. to inactivate the natural inhibiting compounds. The concentration of the thickening agent should be sufficient to maintain the solid matrix during the incubation of the test. Alternatively the solid matrix can also (partly) be formed during the incubation of the test. The thickening agent can be added to the liquid sample using any method known in the art, e.g. as a powder or as a tablet. The thickening agent can be added to the sample prior to addition of the sample to the test or after the sample is added to the test. Alternatively the thickening agent may be part of the test, e.g. as an ingredient of the agar or added onto the agar, e.g. as a tablet or as a powder, before the liquid sample is added to the test. Also a combination of temperature treatment and addition of a thickener is comprised by the invention.

Typically, a solid matrix is a matrix which retains disturbing compounds, for example pigments, but which allows antimicrobial residues in the sample to diffuse out of it.

After addition of the sample the test can be heated to inactivate the natural antimicrobial compounds present in the sample, for example lysozyme. The heating step may also optionally to aid formation of a solid matrix. Preferably, the test is heated for from 2 to 20 minutes at from 70° C. to 100° C. More preferably, the test is heated for from 10 to 15 minutes at from 75° C. to 85° C. or for from 2 to 6 minutes at about 100° C. Any other time/temperature treatment, which is sufficient to inactivate the natural inhibiting compounds of the sample without inactivating the antimicrobial residues to be detected, may be used.

The exact time/temperature requirements depend on e.g. the type of sample (milk, meat or organ juice, urine, egg, blood, etc.); the condition of the sample (e.g. the starting temperature, the volume of the sample); the type of test (e.g. microbial inhibition tests or assays based on selective binders (e.g. antibodies or tracers)); or the microorganism used in the test (e.g. thermophilic or non-thermophilic *Bacillus* or *Streptomyces* species). Of course it should be taken care of that the heat treatment will not inactivate the antimicrobial residues to be detected. The heat treatment can be executed using any method known in the art, e.g. by using an incubator as described below or by heating in a water bath.

After the heat treatment the test is incubated following the instructions of the test manufacturer. The incubation time of the test is dependent on the circumstances. In case of an agar diffusion tests using *Bacillus stearothermophilus* the test is incubated in a water bath or block heater at, for example, from 60° C. to 70° C., preferably at from 62° C. to 65° C. Typically, results may be obtained after from 1.5 to 4 hours, preferably from 2.5 to 3.5 hours. In case of tests using, selective binders, such as antibodies or tracers, the results may be obtained within about 30 minutes.

Conventional microbial inhibition tests suitable for use in the invention, include the commercial products Delvotest®, Premi®Test, BR-Test® (DSM, Holland), the ADM Copan® tests (Copan, Italy) and the CHARM® AIM tests (Charm, USA)). Inactivation of the natural inhibiting compounds present in the liquid sample, and optional formation of a matrix by adding a suitable thickening agent and activation of the spores of the test organism, is preferably achieved by heating for example for from 5 to 15 minutes at for example from 75° C. to 85° C. Alternatively any other temperature/time treatment, which is sufficient to obtain said effects, can be used.

In a further aspect, the invention provides test kits for carrying out the method of the invention. These test kits contain the test and are suitable to execute the method of the invention: add the liquid sample, heat to inactivate the natural inhibiting compounds of the sample, optionally to form a matrix, incubate the test and read the results.

Examples of kits useful for the purpose of the invention are transparent tubes, single or in a set, or combined as a block of translucent material provided with a number of holes shaped therein (incubator). The test kit may contain solidified agar medium, which may be optionally buffered; a test organism (e.g. a strain of *Bacillus* or *Streptococcus*) at sufficient colony forming units; nutrients for growth of said organism; an indicator (e.g. an acid-base or redox indicator); optionally substances to change the sensitivity for certain antimicrobial compounds in a positive or negative way. All ingredients may optionally be added to the test as a separate source, for example as a tablet or paper disc.

The test kits preferably have determined sizes. This is because of the reliability of the test. In case of a test based on agar diffusion technology, preferably tubes are used. The test unit will preferably be high enough to contain an amount of agar medium and a sample corresponding to a height of from 3 to 30 mm, more preferably from 5 to 15 mm. The internal cross-sectional dimension of the test units is preferably from 1 to 30 mm, more preferably from 5 to 15 mm. The test units are preferably closed air tight during storage in which conditions they may be stored for at least several months. Of course any other test unit suitable for executing the method of the invention is included in this invention.

The volume of the agar medium in the test unit is determined by the height of the test unit, the internal cross-sectional dimension of the test unit and the percentage of the volume of the test unit, which is filled with the agar medium. The volume of the agar medium is preferably from 10 µl to 5 ml, more preferably from 100 µl to 1 ml.

Incubators suitable to execute the heat treatments as described in this invention can be constructed in such a way that after placing the test units in the incubator, heat and incubation treatments as described above can be done. The first heat treatment to inactivate the inhibiting compounds and optionally to form solid matrix and/or to activate the spores is executed at a higher temperature, after which the incubation of the test continues at a lower temperature. Optionally after the incubation of the test the incubator can cool down to a temperature sufficient to stop the test.

An example of such an incubator is a block heater in which test units (e.g. ampoules) can be placed. For example in case of a conventional microbial agar diffusion test using a *Bacil-*

*lus stearothermophilus* strain the incubator/block heater may contain a number of holes suitable for placing the test ampoules or test plates (e.g. Delvotest® or Premi®Test) therein. After placing the ampoules or plates the incubator heats the test to a temperature of e.g. from 75° C. to 85° C. for e.g. from 10 to 20 minutes after which the incubator turns to a lower temperature of from 62° C. to 65° C. for from 1.5 to 4 hours (incubation of the test). Of course the exact time/temperature intervals depend on many factors and will differ per type of test. This invention includes all incubators capable to execute a pre-incubation at a certain temperature for a certain period of time directly followed by an incubation at a lower temperature for a certain period of time. Optionally after the incubation of the test the incubator can cool down to a temperature sufficient to stop the test.

The process described in this invention is very simple to carry out, so that persons who perform the test do not have to be specially educated or trained.

All documents mentioned in this application are herein incorporated by reference to the same extent as if each individual application or patent was specifically and individually indicated to be incorporated by reference.

EXAMPLE 1

Inactivation of Natural Inhibiting Compounds Present in a Pre-Urine Sample

Fresh kidneys of 7 negative (negative in the sense of the presence of antibiotics) cows were obtained from a slaughterhouse. To obtain samples for testing for the presence or absence of antimicrobial drug residues, the rosettes of the kidneys were divided into pieces. The pieces were gently squeezed using a garlic press to obtain pre-urine.

The samples were then examined using microbial inhibition test ampoules produced according to the methods described in EP 0005891 with the nutrients present in the agar. The said test is also known as Premi®Test (commercially available from DSM N.V., Delft, The Netherlands).

100 µl of each of the 7 squeezed samples (pre-urine) was added to the test ampoules (in triplicate) and preincubated for 20 minutes at room temperature. It is known that this pre-incubation time is sufficient to let antimicrobial residues (if present in the sample) diffuse into the agar matrix of the test. After this pre-incubation the sample was removed. Finally, the test was incubated in a waterbath at 64° C. following the instructions of the manufacturer. After 185 minutes incubation at 64° C. all 3 samples of 4 animals were still positive (>50%), After 200 minutes all 3 samples of 2 animals were still positive (>30%). These false-positive results were caused by the inhibiting effect of natural inhibiting compounds present in the pre-urine.

100 µl of each of the 7 squeezed samples (pre-urine) was added to the test ampoules and heated for 10 minutes at 80° C. in a waterbath, the ampoules were immediately placed in a waterbath of 64° C. and incubated following the instructions of the manufacturer. After 175 minutes the colour of all tests turned from purple to yellow, indicating that no antimicrobial residues were present.

These results clearly demonstrate that natural inhibiting compounds of the pre-urine inhibit the test leading to false positive results. When the test is executed according to the method described in this invention, i.e. by adding the sample directly to the test, heating the test as described above and incubating the test following the instructions of the producer, the activity of the natural inhibiting compounds was eliminated and no false-positive results were observed.

EXAMPLE 2

Inactivation of Natural Inhibiting Compounds Present in Around-Kidney Sample

This experiment was executed according to the methods described in Example 1, except for the sampling procedure. In this experiment samples from the rosette of the kidney were ground. 100 µl of each of the 7 ground samples (in triplicate) were added to the test ampoules and pre-incubated for 20 minutes at room temperature, after which the samples were removed and the test was incubated as described in Example 1. After 220 minutes all 21 samples were still positive. Moreover, due to discoloration of the test caused by a combination of the presence of natural pigments (e.g. blood) and heating of those pigments, it was not possible to read the results of the test in a proper way.

The experiment was repeated. However now the ground samples were diluted 1:1 with water. After 185 minutes 3 samples were still positive.

Finally, the diluted samples were examined according to the method described in this invention. 100 µl of each of the 7 ground diluted samples was added to the test ampoules, heated for 10 minutes at 80° C. and directly incubated as described in Example 1. After 175 minutes, the colour of all tests turned from purple to yellow, indicating that no antimicrobial residues were present.

These results clearly demonstrate that natural inhibiting compounds of the ground kidney samples inhibit the test leading to false positive results. When the test is executed according to the method described in this invention, by adding the sample directly to the test, heating the test as described above and incubating the test following the instructions of the producer, the activity of the natural inhibiting compounds was eliminated and no false-positive results were observed.

EXAMPLE 3

Inactivation of Natural Inhibiting Compounds Present in an Egg Sample

Samples of 5 eggs (in duplicate), which did not contain antimicrobial residues, were obtained for examination for the presence or absence of antimicrobial residues. A hole of approximately 1-2 cm2 was made in the egg, the egg yolk was pricked and the egg was placed with the hole down on a bottle allowing the egg white and egg yolk to drip into the bottle. After the egg had emptied, the bottle was closed and the sample was homogenized by shaking.

To inactivate the natural inhibiting compounds present in the egg sample, 100 µl of each of the 5 samples was added on Delvotest® ampoules. The test was produced according to the methods described in EP 0005891 with the nutrients present in the agar. After heating for 10 minutes at 80° C. in a waterbath, the ampoules were immediately placed in a waterbath at 64° C. and incubated following the instructions of the producer. After 140 minutes the colour of all tests turned from purple to yellow, indicating that no antimicrobial residues were present.

Control samples were not heated at 80° C. for 10 minutes, but directly placed on the ampoule. These tests remained purple for at least 4 hours.

These results clearly demonstrate that natural inhibiting compounds in the egg sample inhibited the test leading to false-positive results. When the sample was heated as described above, the activity of the natural inhibiting compounds was eliminated and no false-positive results were observed anymore.

EXAMPLE 4

Determination of the Sensitivity of the Delvotest® According to the Method Described in this Invention Using Spiked Samples Egg samples were obtained according to the method described in Example 3. The samples were spiked by adding Penicillin G (0 and 4 ppb) or Sulphadiazine (0 and 100 ppb). The egg samples were added to Delvotest® ampoules (see Example 3) according to the method described in this invention: heated for 10 minutes at 80° C., and then, immediately placed in a waterbath at 64° C. and incubated following the instructions of the manufacturer. The results were read as soon as the colour turned to yellow (after 140 minutes). The samples containing no Penicillin G or Sulphadiazine (o ppb) were negative, while the samples spiked with 4 ppb Penicillin G and 100 ppb sulphadiazine remained purple (positive).

These results clearly demonstrate that the method described in this invention is suitable for detecting antimicrobial residues in egg samples.

EXAMPLE 5

Use of a Thickening Agent in a Kidney Sample

Ground kidney samples were obtained following the methods described in Example 2. However, in this experiment the kidneys were first frozen. It is well known that after freezing of a ground kidney sample many inhibiting compounds are released so that up to now detecting antimicrobial residues using a microbial inhibition test was not possible.

A part of the sample was examined (five fold) using the methods described in Example 2. After 175 minutes all samples were positive, even after 190 minutes 3 samples were positive. Moreover, the results were very difficult to read caused by the presence of natural pigments (e.g. blood).

Another part of the sample was examined as described above. However, the thickening agent bovine albumin (Sigma) was added to the sample (6% and 8%, five fold), after which the sample was added to the tests and heated for 10 minutes at 80° C. After incubation of the tests for 175 minutes at 64° C. all 10 tests were negative, indicating that no antimicrobial residues were present. Moreover, the purple and yellow colours of the test were very bright. Due to the presence of the matrix formed by adding bovine albumin both inhibiting compounds and natural pigments were caught in the matrix.

These results clearly demonstrate that adding a thickening agent to the ground and frozen kidney sample makes it possible to execute the test in a proper way. Both natural inhibiting compounds and natural pigments are caught in the matrix.

EXAMPLE 6

Use of a Thickening Agent in a Chicken Meat Sample

Fresh chicken breast meat of a negative chicken was obtained from a slaughterhouse (negative in the sense of the presence of antibiotics). To obtain meat fluid for further testing pieces of meat were heated for 10 minutes at 64° C. and gently sqeezed using a garlic press. Spiked samples were prepared by adding Amoxicillin (0, 5 and 10 ppb), Oxytetracycline (0, 75 and 100 ppb) or Sulphadiazine (0, 75 and 100 ppb) to the meat juice.

To a part of said samples the thickening agent methylcellulose (4000 c.p.i., Sigma) was added to a final concentration of 1.5%.

100 µl of each sample was added to the Premi®Test ampoules (in duplicate) following the procedure described in Example 1. However, since a thickening agent was added, the pre-incubation step was not required anymore. Also the heating of the samples for 10 minutes at 80° C. was not required for this specific sample.

After 160 minutes the colour of all control tests turned from purple to yellow, indicating that no antimicrobial residues were present. Tests executed with samples containing 5 and 10 ppb of Amoxicillin; 75 and 100 ppb of. Oxytracycline and 75 and 100 ppb of Sulphadiazine remained purple (positive).

In addition a similar experiment was executed. However, now samples containing 10 ppb of Amoxycillin or 200 ppb of Oxytetracycline were prepared and the thickening agent bovine albumine (Sigma) was added to a final concentration of 6%. After 165 minutes the colour of all control tests turned from purple to yellow, while the tests executed with samples containing the antibiotics remained purple.

Due to the presence of the matrix formed by adding methylcellulose or bovine albumine natural pigments present in the meat juice sample were catched in the matrix. As a result of this said tests demonstrated much brighter colours (purple and yellow) as tests executed with samples not containing a thickening agent.

These results clearly demonstrated that adding a thickening agent to the meat juice makes it possible to read the test 20 minutes earlier (no preincubation). Further the test is easier to read, because of brighter colours.

EXAMPLE 7

Use of a Thickening Agent in a Fish Sample

Fresh trouts were obtained from a fish farm. The fish was negative in the sense of the presence of antibiotics.

An experiment similar to the experiment described in Example 6 was executed. As thickening agent methylcellulose was used.

The results were similar as the results described in Example 6, indicating that the method described in this invention is also beneficial for the examination of fish samples.

EXAMPLE 8

Use of a Thickening Agent in a Pre-Urine Sample

The experiment was executed as described in Example 1. However now to a part of the pre-urine sample the thickening agent methylcellulose (4000 c.p.i., Sigma) was added to a final concentration of 1.5%. Also spiked samples were prepared following the method described in Example 6.

After 185 minutes the colour of the control tests, which prior to incubation were heated 10 minutes at 80° C. to inactivate natural inhibiting compounds present in the sample, turned from purple to yellow indicating that no antimicrobial residues were present. Controls which were not heated prior to incubation remained purple for more as 240 minutes (false-positive results).

All test executed with samples containing 5 and 10 ppb of Amoxicillin; 75 and 100 ppb of Oxytetracycline and 75 and 100 ppb of Sulphadiazine remained purple (positive).

Also in this experiment it was demonstrated that due to the presence of the matrix formed by adding methylcellulose natural pigments present in the pre-urine sample were catched in the matrix. As a result of this said tests demonstrated much brighter colours (purple and yellow) as tests executed with samples not containing the thickening agent.

These results clearly demonstrated that adding a thickening agent to the pre-urine makes it possible to read the test 20 minutes earlier (no pre-incubation). Further the test is easier to read, because of brighter colours.

EXAMPLE 9

Use of a Thickening Agent in a Urine Sample

Bovine urine of a negative animal was obtained from a slaughterhouse (negative in the sense of the presence of antibiotics).

Spiked samples were prepared by adding Amoxicillin (0 and 10 ppb) or Oxytetracycline (0 and 200 ppb).

To a part of said samples the thickening agent bovine albumine (Sigma) was added to a final concentration of 6%.

100 µl of each sample was added to the Premi®Test ampoules (in duplo) following the methods described in Example 6.

After 210 minutes the colour of the control tests executed with samples containing bovine albumine turned from purple to yellow. The control samples, to which no thickening agent was added, remained purple (false-positives). Tests executed with samples containing the antibiotics remained purple (positive).

These results clearly demonstrates that due to the presence of the matrix formed by adding bovine, albumine natural inhibitors present in the urine sample were catched in the matrix. Also said tests demonstrated much brighter colours (purple and yellow) as tests executed with samples not containing the thickening agent.

EXAMPLE 10

Use of a Thickening Agent in a Milk Sample

Raw milk samples of negative cows were obtained from a farmer (negative in the sense of the presence of antibiotics).

Spiked samples were prepared by adding Penicillin G to the milk (0, 4 and 6 ppb).

To a part of said samples the thickening agent bovine albumine (Sigma) was added to a final concentration of 6%.

The samples were then examined using microbial inhibition test ampoules produced according to the method described in EP 0005891 with the nutrients in the agar.

100 µl of milk was added to the test ampoules. A part of the test ampoules with the raw milk sample was heated for 10 minutes at 80° C. as described in Example 1. All experiments were executed in five fold. The tests were further incubated following the methods described in Example 1.

After 160 minutes the colour of all control tests, which were heated for 10 minutes at 80° C., turned from purple to yellow indicating that no antimicrobial residues were present. Also all control tests to which bovine albumine was added turned form purple to yellow after 160 minutes. The control tests to which no bovine albumine was added and which were not heated for 10 minutes at 80° C. turned yellow after 185 minutes.

All tests executed with samples containing 4 and 6 ppb of Penicillin G remained purple (positive).

Due to the presence of the matrix formed by adding bovine albumine natural inhibiting compounds present in the raw milk were catched in the matrix. As a result of this the duration of the incubation time of said tests was 25 minutes shorter.

It was also demonstrated that this effect is obtained by heating the test ampoule containing the raw milk sample for 10 minutes at 80° C.

Therefore it can be concluded that with both methods described in this invention natural inhibiting compounds present in the raw milk sample are inactivated: by catching these compounds in the matrix formed by a thickening agent or by inactivation by a heating step.

The invention claimed is:

1. A process for determining the presence or absence of an antimicrobial residue in a sample, which process comprises:
   (i) contacting the sample with a test suitable for determining the presence or absence of an antimicrobial residue in the sample;
   (ii) inactivating any natural disturbing compound present in the sample which is capable of inhibiting the test and which leads to a false positive result absent said inactivating step, by heating said contacted sample and test to a temperature of 75° C. to 85° C. for a sufficient time interval to inactivate the natural disturbing compound that may be present in the sample; followed by
   (iii) incubating the contacted sample and test to determine whether microbial growth occurs, whereby the absence of microbial growth indicates the presence of at least one antimicrobial residue.

2. A process according to claim 1, which further includes contacting said sample with a thickening agent.

3. A process according to claim 2, wherein the thickening agent is a polysaccharide or a protein.

4. A process according to claim 3, wherein the thickening agent is methyl cellulose or bovine albumin.

5. A process according to claim 1, wherein the sample is a foodstuff, an animal body fluid, an animal tissue or an extract thereof.

6. A process according to claim 5, wherein the body fluid is blood, urine, pre-urine, milk, or meat juice.

7. A process according to claim 5, wherein the animal tissue or an extract thereof is muscle, heart, liver or kidney or an extract thereof.

8. A process according to claim 2, wherein the sample is a foodstuff, an animal body fluid, an animal tissue or an extract thereof.

9. A process for determining the presence or absence of an antimicrobial residue in a sample, which process comprises:
   (i) contacting the sample with a test suitable for determining the presence or absence of an antimicrobial residue in the sample;
   (ii) inactivating any natural disturbing compound present in the sample which is capable of inhibiting the test and which leads to a false positive result absent said inactivating step, by heating said contacted sample and test for 10 to 15 minutes to inactivate the natural disturbing compound that may be present in the sample; followed by
   (iii) incubating said contacted sample and test to determine whether microbial growth occurs, whereby the absence of microbial growth indicates the presence of at least one antimicrobial residue.

10. A process according to claim 9, which further includes contacting said sample with a thickening agent.

11. A process according to claim 10, wherein the thickening agent is a polysaccharide or a protein.

12. A process according to claim 11, wherein the thickening agent is methyl cellulose or bovine albumin.

13. A process according to claim 9, wherein the sample is a foodstuff, an animal body fluid, an animal tissue or an extract thereof.

14. A process according to claim 13, wherein the body fluid is blood, urine, pre-urine, milk, or meat juice.

15. A process according to claim 13, wherein the animal tissue or an extract thereof is muscle, heart, liver or kidney or an extract thereof.

16. A process according to claim 10, wherein the sample is a foodstuff, an animal body fluid, an animal tissue or an extract thereof.

\* \* \* \* \*